United States Patent [19]

Geerts et al.

[11] Patent Number: 5,670,589
[45] Date of Patent: Sep. 23, 1997

[54] ORGANOALUMINOXY PRODUCT, CATALYST SYSTEMS, PREPARATION, AND USE

[75] Inventors: Rolf L. Geerts; M. Bruce Welch; Syriac J. Palackal, all of Bartlesville, Okla.; Helmut G. Alt; Bernd Peifer, both of Bayreuth, Germany; Harold R. Deck, Bartlesville, Okla.

[73] Assignee: Phillips Petroleum Company, Bartlesville, Okla.

[21] Appl. No.: 385,515

[22] Filed: Feb. 8, 1995

[51] Int. Cl.$^6$ ............................... C08F 4/642; C07F 5/06
[52] U.S. Cl. .................... 526/160; 526/142; 502/103; 502/104; 502/108; 502/111; 502/113; 502/117; 556/179; 556/175
[58] Field of Search ................... 502/103, 104, 502/108, 111, 113, 117; 556/175, 179; 526/142, 160

[56] References Cited

U.S. PATENT DOCUMENTS

| | | | |
|---|---|---|---|
| 4,530,914 | 7/1985 | Ewen et al. | 502/113 |
| 4,952,540 | 8/1990 | Kioka et al. | 502/9 |
| 4,990,640 | 2/1991 | Tsutsui et al. | 556/181 |
| 5,091,352 | 2/1992 | Kioka et al. | 502/103 |
| 5,106,804 | 4/1992 | Bailly et al. | 502/108 |
| 5,126,301 | 6/1992 | Tsutsui et al. | 502/108 |
| 5,206,401 | 4/1993 | Deavenport et al. | 556/175 |
| 5,283,300 | 2/1994 | Haspeslagh et al. | 526/75 |
| 5,371,260 | 12/1994 | Sangokoya et al. | 556/171 |
| 5,416,229 | 5/1995 | Tran et al. | 556/179 |
| 5,430,892 | 7/1995 | Kuramoto | 526/119 |
| 5,436,305 | 7/1995 | Alt et al. | 526/160 |

FOREIGN PATENT DOCUMENTS 0 586 167 A1   3/1993   European Pat. Off. .

OTHER PUBLICATIONS

C. Janiak et al. (1993) J. Polym. Sci. A 31, 2959–2968.
European Search Report.
Ziemkowska, W. and Pasynkiewics, S.; *XVI International Conference on Organometallic Chemistry* "The Reactions of Trimethylaluminum with Saturated 1,3–Diols" (Jul. 1994) Abstract p. 375.
Ziemkowska, W., et al.; *J. Organometallic Chemistry* "Reactions of Trimethylaluminum with cis–2–buten–1,4–diol" (1994) vol. 465, pp. 93–96.
Pasynkiewicz, S. and Ziemkowska, W.; *Journal of Organometallic Chemistry* "Reactions of trimethylaluminum with 2–[methyl–bis(trimethylsiloxy)silyl]but–2–ene–1,4–diol: synthesis and structure of $[Al(CH_3)]–[OCH_2(SiMe(OSiMe_3)_2C–C(H)CH_2O]_2[Al(CH_3O_2]_2$" (1992) vol. 437, pp. 99–110.

*Primary Examiner*—Mark Nagumo
*Attorney, Agent, or Firm*—Edward L. Bowman

[57] ABSTRACT

In accordance with the present invention, there is provided an organoaluminoxy product prepared by the process comprising reacting an organoaluminoxane with an ene-ol compound. In another embodiment, the organoaluminoxane can be prepared in situ by the process comprising reacting a hydrocarbylaluminum compound, water, and the ene-ol compound. Further there is provided olefin polymerization catalyst systems comprising the organoaluminoxy product and at least one transition metal-containing catalyst. Optionally, the catalyst system is prepolymerized in the presence of at least one olefin to form a prepolymerized catalyst system. Still further there is provided processes for the polymerization of olefins using the catalyst systems.

33 Claims, No Drawings

5,670,589

ORGANOALUMINOXY PRODUCT, CATALYST SYSTEMS, PREPARATION, AND USE

FIELD OF INVENTION

The present invention relates to organoaluminoxy products. The term "organoaluminoxy" as used herein refers to organic compounds containing a plurality of aluminum atoms each bound to at least two oxygen atoms.

BACKGROUND OF THE INVENTION

Organoaluminoxanes are known in the art and can be produced by the partial hydrolysis of hydrocarbyl aluminum compounds. Such aluminoxanes have been found useful in a variety of chemical reactions, including utility as cocatalyst components for polymerization catalysts, especially in metallocene catalyst systems. Such metallocene catalysts have been used in the polymerization of olefins.

An important aspect of olefin polymerization is the activity. By activity is meant the amount or yield of solid polymer that is obtained by employing a given quantity of catalyst in a given amount of time. When the activity is high, catalyst residues do not interfere with the properties of the polymer and therefore the catalyst residues do not need to be removed.

When such catalyst systems are soluble in the polymerization medium, it is generally observed that the resulting polymer has low bulk density. It has also been observed that when particle form polymerizations are carried out in the presence of a soluble metallocene/organoaluminoxane catalyst system, large amounts of polymeric material are formed on the surfaces of the polymerization vessel. This fouling produces an adverse effect on the heat transfer and also results in the need for periodic, if not continuous, cleaning of the reactor. It is therefore necessary to have a catalyst system which will not cause significant amounts of reactor fouling.

It is known that a solid form of organoaluminoxane can be obtained by treating a commercial organoaluminoxane solution with a countersolvent; however, such solids have been found to cause reactor fouling in slurry polymerizations. Reactor fouling is still a problem in slurry polymerization even when a countersolvent is used to precipitate the organoaluminoxane onto an insoluble particulate carrier.

It would therefore be desirable to produce an economical organoaluminoxy product useful as a cocatalyst in a polymerization process free of reactor fouling. It would also be desirable to produce catalyst systems exhibiting high activity.

SUMMARY OF THE INVENTION

An object of the present invention is to provide an organoaluminoxy product useful as a cocatalyst which exhibits high activity when employed in a catalyst system.

Another object of the present invention is to provide an organoaluminoxy product useful as a cocatalyst in a catalyst system which does not produce significant reactor fouling in a particle form polymerization process.

Another object of the present invention is to provide an efficient and economical process for preparing an organoaluminoxy product.

Still another object of the present invention is to provide a polymerization catalyst system comprising at least one transition metal-containing catalyst and an organoaluminoxy product for use in a particle form polymerization process.

Still another object of the present invention is to provide an efficient and economical process for preparing various solid catalyst systems.

Still another object of the present invention is to provide a polymerization process free of significant reactor fouling, especially in a particle form polymerization.

In accordance with the present invention, a process for preparing an organoaluminoxy product useful as a polymerization cocatalyst is provided, the process comprises reacting an organoaluminoxane and an ene-ol compound. Ene-ol as used herein is defined as a compound containing at least one hydroxy group and at least one carbon-carbon double bond. In another embodiment, the organoaluminoxane can be prepared in situ by reacting a hydrocarbyl aluminum compound, water, and the ene-ol compound. Other aspects of the present invention include the organoaluminoxy product thus produced, a catalyst system comprising at least one transition metal-containing catalyst and the organoaluminoxy product, and a polymerization process employing the catalyst system. In a preferred embodiment, the catalyst system is prepolymerized in the presence of an olefin.

DETAILED DESCRIPTION OF THE INVENTION

Organoaluminoxy Product

Various techniques are known for making organoaluminoxanes. One technique involves the controlled addition of water to a hydrocarbylaluminum compound. Suitable hydrocarbylaluminum compounds are represented by the formula $AlR'_3$, wherein each R' is individually selected from hydrocarbyl groups containing 1 to 12 carbon atoms. Another technique involves combining a hydrocarbylaluminum and a hydrocarbon with a compound containing water of adsorption or a salt containing water of crystallization. The present invention is considered applicable to any commercially available organoaluminoxane.

Typically organoaluminoxanes comprise oligomeric, linear and/or cyclic hydrocarbyl aluminoxanes. The organoaluminoxanes are represented by the general formula

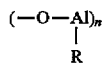

wherein each R is a hydrocarbyl group containing 1 to 12 carbon atoms and n is a number in the range of from 2 to 50, preferably 4 to 40. Preferably R is an alkyl group containing 1 to 8 carbon atoms. Generally aluminoxanes are more active when n is greater than 4, more preferably when n is in the range of from 10 to 40. Typically R is predominantly methyl or ethyl. Preferably at least about 30 mole percent of the repeating groups have an R which is methyl, more preferably at least 50 mole percent, and still more preferably at least 70 mole percent. Generally in the preparation of an organoaluminoxane, a mixture of linear and cyclic compounds is obtained.

Organoaluminoxanes are commercially available in the form of hydrocarbon solutions, generally aromatic hydrocarbon solutions. Typically such organoaluminoxane solutions contain trialkylaluminum compounds as well as the oligomeric organoaluminoxane. The trialkylaluminum compounds generally include those in which the alkyl groups contain 1 to 12 carbon atoms, preferably 1 to 8 carbon atoms.

The organoaluminoxane is reacted with an ene-ol compound to form the organoaluminoxy product, which is an olefinically substituted organoaluminoxane. The ene-ol compound will generally contain from 3 to 24 carbon atoms, preferably from 3 to 20 carbon atoms and more preferably from 3 to 16 carbon atoms. The ene-ol compounds contain at least one hydroxy group and at least one carbon-carbon double bond. Preferably the ene-ol compound is an alcohol. Diols, triols, and tetraols are considered to be within the scope of the invention. Dienes and aromatics containing at least one hydroxy group are also within the scope of the invention. Suitable ene-ol compounds include straight chain, branched, cyclic, or aromatic compounds. Hydrocarbyl aluminum compounds containing at least one hydroxy group and at least one carbon-carbon double bond can also be employed.

Examples of suitable ene-ol compounds include 2-propen-1-ol, 3-buten-1-ol, 4-penten-1-ol, 5-hexen-1ol, 6-hepten-1-ol, 7-octen-1-ol, 5-hexen-1,2-diol, 10-undecen-1-ol, 1,3-heptadien-7-ol, cyclohex-3-en-1-methanol, cyclohex-2-en-1-ol, 4-vinyl-cyclohexanol, 1-hydroxy-4-but-3-enylcyclohexane, 1-hydroxy-3-pent-4-enylcyclohexane, 1-hydroxy-3-methyl-4-but-3-enylcyclohexane, 1-hydroxy-4-but-3-enylbenzene, 1-hydroxy-3-pent-4-enylbenzene, 1-hydroxy-2-methyl-4-but-enylbenzene, p-(oct-4-enyl)phenol, (3-methyl-4-hydroxybenzyl)allylether, 2,4-hexadiene-1-ol, 1,5-hexadien-3-ol, o-allylphenol, o-(1-propenyl)phenol, cinnamyl alcohol, p-(hydroxyethyl)styrene, p-hydroxystyrene, (ethyl)(but-3-enyl)aluminum hydroxide, and mixtures thereof.

The amount of ene-ol compound employed relative to the organoaluminoxane can vary over a wide range depending upon the particular compounds employed and the results desired. Generally the amount of ene-ol compound is in the range of from about 0.001 mole to about 100 moles per mole of organoaluminoxane, preferably about 0.01 moles to about 50 moles, and more preferably from 0.02 moles to 25 moles per mole of organoaluminoxane.

The conditions for reacting the ene-ol compound and the organoaluminoxane can vary widely depending upon the particular compounds employed. Generally the temperature will be in the range of from about −100° C. to about 200° C., preferably from about −20° C. to about 150° C., and more preferably from −10° C. to 100° C. The time of reaction will generally be in the range of from about 1 minute to about 72 hours, preferably about 5 minutes to about 30 hours.

The reaction of the ene-ol compound and the organoaluminoxane can be carried out in any suitable manner. Typically the reactants will be contacted in a suitable liquid diluent. One method involves contacting a hydrocarbon solution of the aluminoxane with a countersolvent to produce a slurry comprising soluble aluminoxane and insoluble aluminoxane and then reacting the resulting slurry with a solution of the ene-ol compound. An example of this method is to mix a toluene solution of methylaluminoxane with hexane to form a slurry and then contacting the ene-ol compound and the slurry.

In another embodiment, the organoaluminoxane can be prepared in situ by reacting a hydrocarbylaluminum compound, water, and the ene-ol compound. The reactants can be combined in any order. The hydrocarbylaluminum compound is represented by the formula AlR'$_3$, wherein each R is individually selected from hydrocarbyl groups containing 1 to 12 carbon atoms, preferably 1 to 8 carbon atoms. Suitable reaction conditions and diluents include those described above for reacting the ene-ol compound and the organoaluminoxane.

It is also within the scope of the present invention to carry out the reaction of the ene-ol compound and the aluminoxane in the presence of a particulate diluent which contains functional groups or is treated to contain functional groups, such as hydroxy or halo groups. For example the particulate diluent can be treated with small amounts of water. Typical particulate diluents include such inorganic materials as silica, alumina, aluminum phosphate, silica-alumina, titania, kaolin, fumed silica, polyethylene, polypropylene, polystyrene, and mixtures thereof.

It is also within the scope of the present invention to prepare the organoaluminoxy product and then combine it with a solution of a trialkylaluminum compound, i.e. trimethylaluminum or others of the type mentioned above. This product can also be contacted with an additional amount of the ene-ol compound. It is believed that this process may provide a method for further increasing the molecular weight of the organoaluminoxy product. The process can be repeated several times to obtain the desired level of molecular weight, particle size, bulk density, or other characteristic that is desired for a particular application. The product can be dried under high vacuum to remove residual solvent which can act as a poison in olefin polymerization processes.

Catalyst Systems

In view of the demonstrated activity of the organoaluminoxy products of the present invention, it is considered that such products will be suitable as catalyst components with any number of olefin polymerization catalysts that have in the past been employed with soluble aluminoxanes.

A catalyst system is prepared by reacting the organoaluminoxy product and at least one transition metal-containing catalyst. The at least one transition metal-containing catalysts are represented by the formula $ML_x$ wherein M is a Group IVB or VB transition metal, x is the valence of the transition metal, and each L is individually selected and is a hydrocarbyl group containing 1 to 12 carbon atoms, alkoxy group containing 1 to 12 carbon atoms, aryloxy group containing 6 to 12 carbon atoms, halogen, hydrogen, amido, or a ligand containing at least one cyclopentadienyl-type group.

Cyclopentadienyl-type groups, as used herein, are unsubstituted cyclopentadienyl, substituted cyclopentadienyl, unsubstituted indenyl, substituted indenyl, unsubstituted fluorenyl, or substituted fluorenyl. The substituents can be any substituent known in the art which does not interfere with the reaction, for example hydrocarbyl groups containing 1 to 12 carbon atoms, alkoxy groups containing 1 to 12 carbon atoms, silyl groups, alkyl halide groups where the alkyl contains 1 to 12 carbon atoms, or halogen. Typical substituents include methyl, ethyl, propyl, butyl, amyl, isoamyl, hexyl, isobutyl, heptyl, octyl, nonyl, decyl, cetyl, 2-ethylhexyl, methoxy, ethoxy, propoxy, butoxy, chlorine, bromine, iodine, phenyl, phenoxy, dimethylsilyl, trimethylsilyl, chloromethyl, chloroethyl, and bromopropyl. Preferably the substituents are alkyl groups containing 1 to 10 carbon atoms, and more preferably 1 to 6 carbon atoms. M is preferably titanium, zirconium, hafnium, or vanadium, more preferably zirconium, titanium, or hafnium, and most preferably M is zirconium.

Some examples of such transition metal-containing olefin polymerization catalysts are disclosed in U.S. Pat. No. 3,242,099, the disclosure of which is incorporated herein by reference. Examples of such transition metal-containing catalysts include titanium trichloride, titanium tetrachloride, titanium tetraethoxide, titanium tetraisopropoxide, titanium tetrabutoxide, titanium tetra-2-ethylhexoxide, titanium tetraiodide, vanadium trichloride, vanadium tetrachloride, zirconium trichloride, zirconium tetrachloride, zirconium tetraethoxide, zirconium tetrabutoxide, and mixtures thereof.

In a particular preferred embodiment, at least one transition metal-containing catalyst is a metallocene compound. Suitable metallocene compounds that can be employed include any metallocene compounds known in the art. Examples of suitable metallocene compounds, their preparation, and their use in polymerization processes are described in detail in U.S. Pat. Nos. 5,091,352; 5,057,475; 5,124,418; 5,191,132; 5,347,026; and EP 524,624 published Jan. 27, 1993, the disclosures of which are incorporated herein by reference.

Metallocene compounds, as used herein, are represented by the above formula $ML_x$, wherein L is as described above, with the proviso that at least one L is a ligand containing at least one cyclopentadienyl-type group. The metallocene compound can contain one, two, three or four cyclopentadienyl-type groups, preferably two. M is as described above and is a Group IVB or VB transition metal, preferably titanium, zirconium, hafnium, or vanadium, more preferably zirconium, and x is the valence of the transition metal.

Typical examples of cyclopentadienyl-type groups include methylcyclopentadienyl, n-butylcyclopentadienyl, di(tert-butyl)cyclopentadienyl, tri(tert-butyl) cyclopentadienyl, pentamethylcyclopentadienyl, 1-methylindenyl, 4,7-dimethylindenyl, 4-methyl-7-(1-propyl)indenyl, 4-ethyl-7-(1-propyl)indenyl, 4-methyl-7-(1-pentyl)indenyl, 4-ethyl-7-(1-pentyl)indenyl, (1-tert-butyl) fluorenyl, (2-ethyl)fluorenyl, (2-tert-butyl)fluorenyl, (4-tert-butyl)fluorenyl, (1-methyl)fluorenyl, (9-methyl)fluorenyl, (9-tert-butyl)fluorenyl, (4-methyl)fluorenyl, 2,7-bis(tert-butyl)fluorenyl, 2,7-bis(tert-butyl)-4-(methyl)fluorenyl, benzyl fluorene, and benzyl indene.

Examples of suitable metallocene compounds include bis(cyclopentadienyl) zirconium dichloride, bis(cyclopentadienyl) zirconium dibromide, bis(cyclopentadienyl) zirconium diiodide, bis(methylcyclopentadienyl) zirconium dichloride, bis(n-butylcyclopentadienyl) zirconium dichloride, bis(cyclopentadienyl) hafnium dichloride, bis(cyclopentadienyl) hafnium dibromide, bis(cyclopentadienyl) hafnium diiodide, bis(methylcyclopentadienyl) hafnium dichloride, bis(n-butylcyclopentadienyl) hafnium dichloride, bis(cyclopentadienyl) titanium dichloride, bis(methylcyclopentadienyl) titanium dichloride, bis(n-butylcyclopentadienyl) titanium dichloride, bis(cyclopentadienyl) zirconium methyl chloride, bis(methylcyclopentadienyl) zirconium ethyl chloride, bis(n-butylcyclopentadienyl) zirconium phenyl chloride, bis(cyclopentadienyl) hafnium methyl chloride, bis(methylcyclopentadienyl) hafnium ethyl chloride, bis(n-butylcyclopentadienyl) hafnium phenyl chloride, bis(cyclopentadienyl) titanium methyl chloride, bis(methylcyclopentadienyl) titanium ethyl chloride, bis(n-butylcyclopentadienyl) titanium phenyl chloride, bis(cyclopentadienyl) zirconium dimethyl, bis(methylcyclopentadienyl) zirconium dimethyl, bis(n-butylcyclopentadienyl) zirconium dimethyl, bis(cyclopentadienyl) hafnium dimethyl, bis(methylcyclopentadienyl) hafnium dimethyl, bis(n-butylcyclopentadienyl) hafnium dimethyl, bis(cyclopentadienyl) titanium dimethyl, bis(methylcyclopentadienyl) titanium dimethyl, bis(n-butylcyclopentadienyl) titanium dimethyl, pentamethylcyclopentadienyl titanium trichloride, pentaethylcyclopentadienyl zirconium trichloride, pentaethylcyclopentadienyl hafnium trichloride, bis(pentamethylcyclopentadienyl) titanium diphenyl, bis(indenyl) hafnium dichloride, bis(indenyl) titanium diphenyl, bis(indenyl) zirconium dichloride, bis(fluorenyl) zirconium dichloride, bis(1-methylfluorenyl) zirconium dichloride, and mixtures thereof.

It is also within the scope of the present invention to employ metallocene compounds containing bridged ligands, where two of the L groups are cyclopentadienyl-type groups which are bonded together by a suitable bridging group containing carbon, silicon, germanium, or tin. The bridging group can be substituted or unsubstituted. The bridge substituents can be, for example hydrocarbyl groups containing 1 to 12 carbon atoms, alkoxy groups containing 1 to 12 carbon atoms, or halogen. Excellent results have been obtained with bridged ligands and they are preferred.

Some examples of such bridged ligands include (9-fluorenyl)(cyclopentadienyl)methane, (9-fluorenyl)(cyclopentadienyl)dimethylmethane, 1,2-bis(1-indenyl)ethane, 1,2-bis(9-fluorenyl)ethane, 1-(9-fluorenyl)-2-(cyclopentadienyl)ethane, (9-fluorenyl)(1-indenyl)methane, 1-(9-fluorenyl)-1-(cyclopentadienyl)cyclopentane, (9-fluorenyl)(cyclopentadienyl)silane, bis(9-fluorenyl) diphenylsilane, (9-fluorenyl)(cyclopentadienyl) dimethylsilane, (9-fluorenyl)(cyclopentadienyl) dimethylgermane, bis(9-fluorenyl)dimethylstannane, 1-(9-fluorenyl)-3-(cyclopentadienyl)propane, (9-fluorenyl)(1-indenyl)methane, bis(9-fluorenyl)dimethylmethane, (methylcyclopentadienyl)(9-fluorenyl)methane, (n-butylcyclopentadienyl) (1-indenyl)methane, 1-(di(tert-butyl)cyclopentadienyl)-2-(9-fluorenyl)ethane, 1-(1-methylindenyl)-1-(9-(4-methylfluorenyl)ethane, (4,7-dimethylindenyl) (9-fluorenyl)silane, (cyclopentadienyl)(9-(1-tert-butylfluorenyl))methane, (cyclopentadienyl)(9-(2-ethylfluorenyl))methane, (indenyl) (9-(4-tert-butylfluorenyl))methane, (cyclopentadienyl)(9-(2,7-bis(tert-butyl)(fluorenyl))ethane and (cyclopentadienyl)(9-(2,7-bis(tert-butyl)-4-(methyl)(fluorenyl))methane and the mixtures thereof.

It is also within the scope of the invention to employ metallocene compounds containing ligands containing unsaturated substituents. Typical examples of bridged ligands containing unsaturated substituents include 1-(9-(2-vinyl)fluorenyl)-2-(9-fluorenyl)ethane, (9-(2-vinyl) fluorenyl)(cyclopentadienyl)methane, 1-(9-(2-vinyl) fluorenyl)-2-(cyclopentadienyl)ethane, (9-(2-vinyl) fluorenyl)(1-indenyl)methane, 1-(9-(2-vinyl)fluorenyl)-1-(cyclopentadienyl)cyclopentane, (9-(2-vinyl)fluorenyl) (cyclopentadienyl)(1-cyclo-3-hexenyl)methane, (9-(2-vinyl)fluorenyl)(cyclopentadienyl)dimethylmethane, (9-fluorenyl)[1-(3-vinyl)phenylcyclopentadienyl] diphenylmethane, (9-(2,7-divinyl)fluorenyl)(1-(3-methyl) cyclopentadienyl)dimethylmethane, (9-(2-vinyl)fluorenyl) (cyclopentadienyl)silane, (9-(2-vinyl)fluorenyl) (cyclopentadienyl)dimethylsilane, (9-(2-vinyl)fluorenyl)(9-fluorenyl)diphenylsilane, (9-(2-vinyl)fluorenyl) (cyclopentadienyl)dimethylgermane, (9-(2-vinyl)fluorenyl) (fluorenyl)dimethylstannane, 1-(9-(2-vinyl)fluorenyl)-3-(cyclopentadienyl)propane, 1-(9-fluorenyl)-1-(methyl)-1-(1-(2-vinylcyclopentadienyl)ethane, (9-(2,7-diphenylfluoroenyl)(1-(3-vinyl)cyclopentadienyl) diphenylmethane, bis(9-(1-methyl-4-vinyl)fluorenyl) diphenylmethane, (fluorenyl)(cyclopentadienyl)methyl)(1-

(4-vinyl)phenyl)methane, (1-butenyl)(methyl)(cyclopentadienyl)(fluorenyl)methane, and the mixtures thereof.

It is also within the scope of the invention to employ metallocene compounds containing two cyclopentadienyl-type groups where only one of such groups is bonded to the transition metal. An example is of such metallocene compounds is (9-fluorenyl)(cyclopentadienyl) methane zirconium trichloride.

Suitable metallocene compounds also include those metallocene compounds where one L is a ligand containing one cyclopentadienyl-type group bonded to a bridging group containing carbon, silicon, germanium, or tin and the bridging group is also bonded to a group containing a heteroatom selected from nitrogen, phosphorous, sulfur, or oxygen. Examples of such metallocene compounds are disclosed in U.S. Pat. No. 5,057,475, the disclosure of which is herein incorporated by reference.

It is also within the scope of the invention to employ mixtures of transition metal-containing catalysts. For example, mixtures of metallocene compounds and non-metallocene transition metal-contain employed. The term employed. The term "non-metallocene" as used herein is defined as a which does not contain a cyclopentadienyl-type group.

Another example is to employ a mixture of metallocene compounds, for example a mixture of bridged and unbridged metallocene compounds. The term "unbridged" as used herein refers to cyclopentadienyl-type groups which are not connected by a bridging group. When employing mixtures of bridged and unbridged metallocene compounds, the bridged metallocene compound will generally be present in an amount in the range of from about 0.001 mole to about 1000 moles per mole of unbridged metallocene compound, preferably from about 0.01 mole to about 100 moles per mole of unbridged metallocene compound. Another example would be a mixture of a metallocene compound and a transition metal halide, such as zirconium or titanium tetrahalides.

When preparing the catalyst system, the amount of organoaluminoxy product relative to the transition metal-containing catalyst can vary broadly depending upon the particular catalyst selected and the results desired. Typically, the organoaluminoxy product will be present in the amount in the range of about 0.1 mole to about 10,000 moles per mole of transition metal-containing catalyst, preferably about 1 moles to about 1000 moles, and more preferably 5 moles to 1000 moles.

In a preferred embodiment, the catalyst system is prepolymerized at least once in the presence of a limiting amount of at least one olefin. The prepolymerized catalyst system can be washed and prepolymerized again with at least one olefin. Generally the olefin will contain from 2 to 24 carbon atoms, preferably from 2 to 18 carbon atoms, and more preferably from 2 to 12 carbon atoms. Suitable olefins include ethylene, propylene, 1-butene, 1-pentene, 2-pentene, 3-methyl-1-butene, 4-methyl-1-pentene, 1-hexene, 2-hexene, cyclohexene, 1-heptene, dienes such as 1,3-butadiene, cyclopentene, cyclooctene, norbornene, tetracyclododecene, and mixtures thereof. Ethylene is preferred.

Typically the prepolymerization will be conducted at relatively low temperature and pressure. Generally the prepolymerization will be conducted at a temperature in the range of about −100° C. to about 200° C., preferably in the range of about −40° C. to about 100° C. The prepolymerized solid catalyst system can be filtered, washed, and dried under vacuum.

The amount of prepolymer can vary broadly but generally will be in the range of from about 1 to about 95 weight percent based on the total prepolymerized catalyst system, preferably in the range of about 5 to about 80 weight percent. Preferably the prepolymer will be present in an amount sufficient to form a solid catalyst system.

Other cocatalysts can also be used in combination with the catalyst systems. Examples of suitable cocatalysts include any of those organometallic cocatalysts which have in the past been employed in conjunction with transition metal-containing olefin polymerization catalysts. Some typical examples include organometallic compounds of metals of Groups IA, IIA, and IIIB of the Periodic Table. Examples of such compounds include organometallic halide compounds, organometallic hydrides, and metal hydrides. Some specific examples include triethylaluminum, triisobutylaluminum, diethylaluminum chloride, diethylaluminum hydride, and the like. Other examples of known cocatalysts include the use of compounds capable of forming a stable non-coordinating counter anion, such as disclosed in U.S. Pat. No. 5,155,080, .e.g. using triphenyl carbenium tetrakis(pentafluorophenyl)boronate or tris (pentaflurophenyl)boron. Another example would be the use of a mixture of trimethylaluminum and dimethylfluoroaluminum such as disclosed by Zambelli et, *Macromolecules*, 22, 2186 (1989).

Polymerization Processes

The catalyst system is useful in the polymerization of olefin compounds. The catalyst system is contacted with at least one olefin under polymerization conditions. A variety of olefin compounds are suitable for use as monomers in the polymerization process of the present invention. Olefins which can be employed include linear, branched, cyclic, and aromatic olefins. Olefins having 2 to 24 carbon atoms are most often used, preferably 2 to 18 carbon atoms. Ethylene and propylene are especially preferred. Often a second or third such olefin (comonomer) can be employed. Typical polymerizable olefins include ethylene, propylene, 1-butene, 1-pentene, 2-pentene, 3-methyl-1-butene, 4-methyl-1-pentene, 1-hexene, 2-hexene, cyclohexene, 1-heptene, styrene, cyclopentene, cyclooctene, norbornene, tetracyclododecene, methyltetracyclododecene, and dienes such as 1,3-butadiene, and mixtures thereof.

The reaction conditions for reacting the at least one olefin and the catalyst system can vary broadly depending on the olefin employed, and are those sufficient to polymerize the olefins. Generally the temperature is in the range of about 20° C. to about 300° C., preferably in the range of 50° C. to 150° C. The pressure is generally in the range of from about 0.5 MPa to about 5.0 MPa (70–725 psi).

The polymerization processes according to the present invention can be performed either batchwise or continuously. The olefin, the at least one transition metal-containing catalyst, and the organoaluminoxy product can be contacted in any order. In a typical batch process, for example, a stirred autoclave is prepared by first purging with nitrogen and then charging with a suitable diluent, such as isobutane for example. Either the transition metal-containing catalyst or the organoaluminoxy product cocatalyst can be charged to the reactor first or the catalyst and the cocatalyst can be charged simultaneously. As discussed above, it is especially preferred that the organoaluminoxy product and the transition metal-containing catalyst be prepolymerized in the presence of a small amount of at least one olefin under relatively mild conditions to form a prepolymerized catalyst system. Generally a diluent, such as isobutane, is added to the reactor. The reactor is heated to the desired reaction temperature and olefin, such as ethylene, is then admitted and maintained at a partial pressure within a range of from about 0.5 MPa to about 5.0 MPa (70–725 psi) for best results. At the end of the designated reaction period, the polymerization reaction is terminated and the unreacted olefin and diluent can be vented. The reactor can be opened and the polymer can be collected as a free-flowing white solid and dried to obtain the product.

The present invention is particularly useful in a gas phase particle form or slurry type polymerization. A particularly preferred slurry type polymerization involves a continuous loop reactor which is continuously charged with suitable quantities of diluent, catalyst, cocatalyst, and polymerizable compounds in any desirable order. Typically the polymerization will include an olefin comonomer and optionally hydrogen. Generally the slurry polymerization would be conducted at a temperature in the range of about 60° C. to about 100° C., although higher and lower temperatures can be used. The reaction product can be continuously withdrawn and the polymer recovered as appropriate, generally by flashing the diluent and unreacted monomers and drying the resulting polymer.

The olefin polymers produced with the present invention are useful in preparing articles prepared by conventional polyolefin processing techniques, such as injection molding, rotational molding, film extrusion, pipe extrusion, and blow molding.

The following examples will serve to show the present invention in detail by way of illustration and not by way of limitation.

EXAMPLE 1

A catalyst system was prepared employing an organoaluminoxy product and the metallocene compound bis (fluorenyl)ethane zirconium dichloride. The organoaluminoxy product was prepared by reacting allyl alcohol and methylaluminoxane (MAO) as described below.

The organoaluminoxy product was prepared by reacting 0.5 mL allyl alcohol (7.54 mmol) in 10 mL toluene with 10.0 mL 30 weight % MAO (40.5 mmol) in 50 mL toluene which had been cooled in an ice bath. The thus produced organoaluminoxy product was stirred for one hour and then 5 mg bis(fluorenyl)ethane zirconium dichloride was added. The color of the solution turned from green to violet and then to blue. The solution was prepolymerized using 0.2 bar ethylene at room temperature for one hour. Prepolymerized solid catalyst system as blue precipitate was formed during the prepolymerization.

EXAMPLE 2

Example 2 demonstrates the effectiveness of employing a catalyst system containing a vinyl-containing metallocene compound for polymerizing ethylene polymers and ethylene/hexene copolymers. A catalyst system was prepared employing an organoaluminoxy product and (but-3-enyl)(methyl)(cyclopentadienyl)(fluorenyl)methane zirconium dichloride. The organoaluminoxy product was prepared by reacting 5-hexen-1,2-diol and MAO as described below.

To 50 mL 1.7M MAO in toluene (83.5 mmol) was added dropwise, 0.75 g 5-hexen-1,2-diol (6.42 mmol) in 10 mL toluene. The ene-diol was added over a 2 hour period with vigorous stirring. The solution was stirred for 64 hours. To a 15 mL aliquot of the thus produced organoaluminoxy product was added 35 mL toluene. To this stirred slurry was added 33 mg of orange (but-3-enyl)(methyl) (cyclopentadienyl)(fluorenyl)methane zirconium dichloride to produce the catalyst system. The solution turned red and was stirred for one half hour. To the stirred solution containing the catalyst system was added one atmosphere ethylene. The color gradually faded and an orange slurry was produced. The thus produced prepolymerized solid catalyst system was filtered under anhydrous conditions leaving a pale orange solid which was washed with 3×10 mL toluene and then with 20 mL pentane and then dried under vacuum for two hours. The yield of the thus produced prepolymerized solid catalyst system was 3 g.

Ethylene was polymerized in a 1-gallon stirred autoclave reactor under particle form conditions employing 0.1360 g of the thus prepared catalyst system in 2 liter isobutane. The polymerization was conducted at a temperature of 70° C., a pressure of 341 psig, in the presence of hydrogen for one hour. After the polymerization was complete, the isobutane was removed and the polymer collected as a dry fluff. The polymer yield was 187 g. The polymer density was 0.9445 g/cc measured according to ASTM D 1505. The melt index was 0.82 g/10 min. measured according to ASTM 1238. Condition E and the high load melt index was 17.49 g/10 min. measured according to ASTM 1238. Condition F.

Ethylene and hexene were copolymerized as described above with the exception that the temperature was 90° C., the pressure was 450 psig, the amount of prepolymerized catalyst system was 0.1131 g, and 90 g of hexene was employed. The polymer yield was 31.6 g, the melt index was 17.24 g/10 min., and the density was 0.8990 g/cc.

EXAMPLE 3

Example 3 demonstrates the effectiveness of inventive catalyst systems for polymerizing ethylene. The catalyst systems contained organoaluminoxy products prepared with various ene-ol compounds In Run 301, a catalyst system was prepared containing an unreacted methylaluminoxane. The control was prepared as follows. To a 150 mL serum vial was added 10 mL 1.7M MAO (17 mmol), 50 mL toluene, and 7 mg of the metallocene compound bis(n-butylcyclopentadienyl) zirconium dichloride dissolved in 10 mL toluene to produce the catalyst system. The reaction mixture was stirred with a stirring bar and the colorless solution turned a faint yellow. The solution was cooled to about 5° C. while stirring in an ice bath. The vial was purged with ethylene for 1 minute through the septum cap using a needle vent. The vial was then pressurized to about 40 psig with ethylene while stirring the solution for one half hour. The vial was repressurized to 40 psig with ethylene and stirred for another half hour to produce the prepolymerized catalyst system. The solution was placed in a dry box and the solids were collected on a filter, extracted with 2×25 ml toluene, washed with 25 mL toluene, and dried. A white, hard, chunky powder was obtained. The yield was 0.86 g prepolymerized catalyst system.

In preparing the catalyst systems in Runs 302 to 304, the process described above was repeated with the exception that predetermined amounts of the indicated ene-ols were added dropwise to the indicated amount of MAO in toluene and stirred prior to the addition of the metallocene compound. Gas evolution was observed during the reaction.

Ethylene polymerizations were conducted in a 1-gallon stirred autoclave reactor under particle form conditions. The polymerizations were conducted at the indicated temperature and pressure in 2 liters isobutane in the presence of hydrogen for about one hour. After the polymerization was complete, the isobutane was removed and the polymer collected as a dry fluff. The results are tabulated in the Table below.

In the Table below:

MAO is the millimoles methylaluminoxane reacted with the indicated ene-ol compound.

Ene-ol is the ene-ol compound in millimoles reacted with the MAO to produce the organoaluminoxy product.

Metallocene is the milligrams bis(n-butylcyclopentadienyl) zirconium dichloride reacted with the organoaluminoxy product.

Catalyst is the grams prepolymerized catalyst system employed in the polymerization process.

PE is the polyethylene yield in grams.

Activity is the grams polyethylene per gram catalyst hour.

TABLE 1

| Run | MAO mmol | Ene-ol mmol | Metallocene mg | Catalyst g | PE g | Activity g PE/g catalyst hr |
|---|---|---|---|---|---|---|
| 301 | 17 | none 0 | 7 mg | 0.3912 * | 34 | 87 |
| 302 | 17 | 10-undecen-1-ol 2.27 mmol | 7 mg | 0.3855 * | 646 | 1680 |
| 303 | 34 | 5-hexen-1-ol 4.5 mmol | 1.4 mg | 0.4855 ** | 261 | 538 |
| 304 | 34 | 5-hexen-1,2-diol 4.5 mmol | 1.4 mg | 0.4664 ** | 150 | 324 |

*Polymerization temperature 70° C., a partial pressure hydrogen and isobutane of about 150 psig, and a total pressure of about 340 psig.
**Polymerization temperature 90° C., a partial pressure hydrogen and isobutane of about 230 psig, and a total pressure of about 450 psig.

The results in the table above demonstrate improved activity when employing a catalyst system where the organoaluminoxane has been reacted with an ene-ol compound.

That which is claimed is:

1. A process for preparing a solid catalyst system comprising
    reacting an organoaluminoxane and an ene-ol compound wherein said organoaluminoxane is represented by the formula

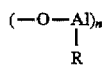

wherein each R is a hydrocarbyl group containing 1 to 12 carbon atoms and n is a number in the range of from 2 to 50;and
    wherein said ene-ol compound contains at least one hydroxy group, at least one carbon-carbon double bond, and contains from 3 to 24 carbon atoms,
    (b) combining the product of step (a) with at least one transition metal-containing catalyst to form a catalyst system,
    (c) prepolymerizing said catalyst system in a liquid in the presence of at least one olefin containing 2 to 18 carbon atoms,
    (d) separating the resulting solid catalyst from the liquid and the components contained in the liquid to yield said solid catalyst system,
    wherein said at least one transition metal-containing catalyst is represented by the formula

wherein M is a Group IVB or VB transition metal, x is the valence of the transition metal, and each L is individually selected and is a hydrocarbyl group containing 1 to 12 carbon atoms, alkoxy group containing 1 to 12 carbon atoms, aryloxy group containing 6 to 12 carbon atoms, halogen, hydrogen, amido, or a ligand containing at least one cyclopentadienyl-type group, and
    wherein said cyclopentadienyl-type group is unsubstituted cyclopentadienyl, substituted cyclopentadienyl, unsubstituted indenyl, substituted indenyl, unsubstituted fluorenyl, or substituted fluorenyl, wherein the substituents are hydrocarbyl groups containing 1 to 12 carbon atoms, alkoxy groups containing 1 to 12 carbon atoms, silyl groups, alkyl halide groups where the alkyl contains 1 to 12 carbon atoms, or halogen.

2. A process according to claim 1 wherein said ene-ol compound contains from 3 to 20 carbon atoms.

3. A process according to claim 2 wherein said ene-ol compound contains from 3 to 16 carbon atoms.

4. A process according to claim 3 wherein said ene-ol compound comprises 2-propen-1-ol, 5-hexen-1-ol, 5-hexen-1,2-diol, or 10-undecen-1-ol.

5. A process according to claim 2 wherein said ene-ol compound is present in an amount in the range of from about 0.001 mole to about 100 moles per mole of organoaluminoxane.

6. A process according to claim 5 wherein said ene-ol compound is present in an amount in the range of from 0.01 moles to about 50 moles per mole of organoaluminoxane.

7. A process according to claim 6 wherein said ene-ol is present in an amount in the range of from 0.02 moles to about 25 moles per mole of organoaluminoxane.

8. A process according to claim 5 wherein said reacting is conducted a temperature in the range of from about −100° C. to about 200° C.

9. A process according to claim 8 wherein said reacting is conducted at a temperature in the range of about −20° C. to about 150° C.

10. A process according to claim 9 wherein said reacting is conducted at a temperature in the range of from −10° C. to 100° C.

11. A process according to claim 1 wherein said at least one transition metal-containing catalyst comprises a metallocene compound where at least one L is a ligand containing at least one cyclopentadienyl-type group.

12. A process according to claim 11 wherein said catalyst system comprises a mixture of said metallocene compound and a non-metallocene transition metal-containing catalyst.

13. A process according to claim 11 wherein said ligand contains two cyclopentadienyl-type groups and only one is bonded to the transition metal.

14. A process according to claim 11 wherein two L groups are ligands containing cyclopentadienyl-type groups.

15. A process according to claim 14 wherein said ligands are bonded together by a bridging group which contains carbon, silicon, germanium, or tin to form a bridged metallocene compound.

16. A process according to claim 15 wherein said catalyst system comprises a mixture of said bridged metallocene compound and a non-bridged metallocene compound.

17. A process according to claim 1 wherein said prepolymerizing is conducted at a temperature in the range of from about −100° C. to about 200° C.

18. A process according to claim 17 wherein said at least one olefin contains 2 to 12 carbon atoms.

19. A process according to claim 18 wherein said at least one olefin comprises ethylene.

20. A process according to claim 17 wherein said organoaluminoxy product is present in an amount in the range of about 0.1 mole to about 10,000 moles per mole of transition metal containing catalyst.

21. A process according to claim 20 wherein said organoaluminoxy product is present in an amount in the range of about 1 mole to about 1000 moles per mole of transition metal containing catalyst.

22. A process according to claim 21 wherein said catalyst system is recovered, washed, and dried under vacuum.

23. An olefin polymerization catalyst system comprising the solid catalyst system produced by the process of claim 1.

24. A catalyst system according to claim 23 wherein at least one L is a ligand containing at least one cyclopentadienyl-type group.

25. A catalyst system according to claim 24 wherein said at least one transition metal-containing catalyst comprises bis(n-butylcyclopentadienyl) zirconium dichloride, bis (fluorenyl)ethane zirconium dichloride, or (but3-enyl) (methyl(cyclopentadienyl)(fluorenyl)methane zirconium dichloride.

26. A catalyst system according to claim 23 wherein said organoaluminoxane is represented by the formula

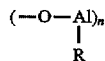

wherein each R is a hydrocarbyl group containing 1 to 12 carbon atoms and n is a number in the range of from 4 to 50;

wherein said ene-ol compound comprises 2-propen-1-ol, 5-hexene-1-ol, 5-hexene-1,2-diol, or 10-undecen-1-ol; and wherein said at least one transition metal-containing catalyst comprises bis(n-butylcyclopentadienyl) zirconium dichloride, (1-butenyl)(methyl) (cyclopentadienyl) (fluorenyl) methane zirconium dichloride, bis (fluorenyl)ethane zirconium dichloride, or mixtures thereof.

27. A catalyst system according to claim 26 wherein said organoaluminoxane comprises methylaluminoxane.

28. A polymerization process comprising contacting at least one olefin under polymerization conditions with the catalyst system of claim 23, wherein said olefin contains from 2 to 24 carbon atoms.

29. A polymerization process according to claim 28 wherein said at least one olefin contains from 2 to 18 carbon atoms.

30. A polymerization process according to claim 29 wherein said olefin comprises ethylene or propylene.

31. A polymerization process according to claim 30 where said polymerization conditions include a temperature in the range of from about 20° C. to to 200° C.

32. A polymerization process according to claim 30 where said polymerization is conducted under particle form conditions.

33. An organoaluminoxy product useful as a polymerization cocatalyst, said organoaluminoxy product comprising the reaction product of an organoaluminoxane and an ene-ol compound:

wherein said organoaluminoxane is represented by the formula

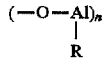

wherein each R is a hydrocarbyl group containing 1 to 8 carbon atoms and n is a number in the range of from 2 to 50;and wherein said ene-ol compound contains at least one hydroxy group, at least one carbon-carbon double bond, and contains from 2 to 24 carbon atoms.

* * * * *

UNITED STATES PATENT AND TRADEMARK OFFICE
CERTIFICATE OF CORRECTION

PATENT NO.  : 5,670,589

DATED       : September 23, 1997

INVENTOR(S) : Rolf L. Geerts et al

It is certified that error appears in the above-identified patent and that said Letters Patent is hereby corrected as shown below:

Column 11, line 42 before "reacting", please insert ---(1)---.

Column 13, line 38, please delete "(but3-enyl)" and insert therefor ---(but-3-enyl)---.

Column 14, line 22, please delete "claim 29" and insert therefor ---claim 28---.

Signed and Sealed this

Sixteenth Day of December, 1997

Attest:

BRUCE LEHMAN

Attesting Officer

Commissioner of Patents and Trademarks